United States Patent [19]

Dumont et al.

[11] 4,112,093

[45] Sep. 5, 1978

[54] STIMULATING DOPAMINERGINIC ACTIVITY

[75] Inventors: Claude Dumont, Nogent-sur-Marne; Claude Oberlander, Paris, both of France

[73] Assignee: Roussel Uclaf, Paris, France

[21] Appl. No.: 807,068

[22] Filed: Jun. 16, 1977

[30] Foreign Application Priority Data

Jun. 23, 1976 [FR] France .............................. 76 19088

[51] Int. Cl.$^2$ .......................................... A61K 31/495
[52] U.S. Cl. ................................................. 424/250
[58] Field of Search ................................ 424/250, 263

[56] References Cited

PUBLICATIONS

J. Med. Chem., vol. 6 (1963), pp. 541–544.

*Primary Examiner*—Stanley J. Friedman
*Attorney, Agent, or Firm*—Hammond & Littell

[57] ABSTRACT

Novel dopaminerginic compositions comprised of an dopaminergically effective amount of at least one member of the group consisting of N-(3,4-methylenedioxybenzyl)-N'-(2-pyridyl)-piperazine and its non-toxic, pharmaceutically acceptable acid addition salts and an inert pharmaceutical carrier and to a novel method of treating the symptoms of Parkinson disease.

3 Claims, No Drawings

STIMULATING DOPAMINERGINIC ACTIVITY

STATE OF THE ART

An article in J. Med. Chem., Vol. 6 (1963), p. 541–544 describes various benzyl-piperazine derivative having a widely diverse degree of cardiovascular properties and it is stated that compound XVIII which is N-(3,4-methylenedioxybenzyl)-N'-(2-pyridyl)-piperazine possesses only weak cardiovascular properties. Outside of these properties, there is no mention in the article of other physiological properties and therefore the said product is not described as being present in a medicament.

OBJECTS OF THE INVENTION

It is an object of the invention to provide novel dopaminergic stimulating compositions.

It is another object of the invention to provide a novel method of treating symptoms of Parkinson disease in warm-blooded animals.

These and other objects and advantages of the invention will become obvious from the following detailed description.

THE INVENTION

The novel dopaminergic compositions of the invention are comprised of an dopaminergically effective amount of at least one member of the group consisting of N-(3,4-methylenedioxy-benzyl)-N'-(2-pyridyl)-piperazine and its non-toxic, pharmaceutically acceptable acid addition salts and an inert pharmaceutical carrier. The said dopaminergic stimulating properties of the said composition is in a field completely removed from the cardiovascular field.

The activity of the present product has been compared with a derivative of a related chemical structure, piribedil and in the test used, the product of the invention has a more marked activity then piribedil. Moreover, the product of the invention possesses very weak cardiovascular properties while piribedil has been reported as possessing such properties [Experientia, Oct. 15, 1975, p. 1204].

Examples of suitable acids for the formation of non-toxic, pharmaceutically acceptable acid addition salts are inorganic acids such as hydrochloric acid, hydrobromic acid, hydroiodic acid, nitric acid, sulfuric acid and phosphoric acid; organic carboxylic acids such as acetic acid, formic acid, benzoic acid, maleic acid, fumaric acid, succinic acid, tartaric acid, citric acid, oxalic acid, glyoxylic acid and aspartic acid; alkane sulfonic acids such as methane sulfonic acid and aryl sulfonic acids such as benzene sulfonic acid.

The compositions are useful for the treatment of neurological syndromes of extrapyramidal origin, treatment of Parkinson disease, of post-encephalitic parkinsonian syndromes and parkinsonian syndromes of arteriosclerous origin or toxic etiology.

The compositions of the invention may be in the form of tablets, dragees, gelules, capsules, granules, suppositories, and injectable solutions or suspensions. Examples of suitable excipients or inert pharmaceutical carriers are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

As indicated in J. Med. Chem., Vol. 6 (1963), p. 514–544, N-(3,4-methylenedioxy-benzyl)-N'-(2-pyridyl)-piperazine is obtained in an 83% yield by reaction of N-(2-pyridyl)-piperazine and 3,4-methylenedioxy-benzyl chloride and after crystallization from isopropanol has a melting point of 84° c. Since the product has a basic character, the acid addition salts can be prepared by reacting the free base with approximately stoichiometric proportions of an inorganic or organic base.

The novel method of the invention for the treatment of the symptoms of Parkinson disease in humans comprises administering to humans an amount effective to treat the said symptoms of at least one compound selected from the group consisting of N-(3,4-methylenedioxy-benzyl)-N'-(2-pyridyl)-piperazine and its non-toxic, pharmaceutically acceptable acid addition salts. The compounds may be administered orally, rectally, or parenterally and the usual useful dose is 0.1 to 2 mg/kg by oral route in man.

In the following examples there are described several preferred embodiments to illustrate the invention. However, it is to be understood that the invention is not intended to be limited to the specific embodiments.

EXAMPLE 1

Tablets were prepared containing 15 mg of N-(3,4-methylenedioxy-benzyl)-N'-(2-pyridyl)-piperazine and sufficient excipient to obtain a final tablet weight of 200 mg.

EXAMPLE 2

An injectable solution was prepared containing 5 mg of N-(3,4-methylenedioxy-benzyl)-N'-(2-pyridyl)-piperazine and sufficient sterile aqueous excipient for a final volume of 2 ml.

PHARMACOLOGICAL STUDY

The test products were studied on rats after unilateral injury of black substance by the method described by Ungerstedt [Acta. Physiol. Scan., Suppl. 367 (1971), p. 69–73] in which 8 rats in each group received an injection in the right black substance of 8 $\beta$g of 6-hydroxy-dopamine dissolved in 4 $\mu$l of aqueous 9% sodium chloride containing 1 mg per ml of ascorbic acid at a rate of 1 $\mu$l per minute. The administration of apomorphine hydrochloride to the animals caused contralateral rotations with respect to the lesion and dexamphethamine sulfate caused ipsilateral rotations. The administration, to these same rats, of 25 mg/kg per os of N-(3,4-methylenedioxy-benzyl)-N'-(2-pyridyl)-piperazine (product A) and piribedil caused controlateral rotations and the results are reported in Table I.

TABLE I

| Product | Dose in mg/kg per os | Contraleral rotations per rat in first hour after administration |
|---|---|---|
| A | 25 | 165 ± 48 |
| Piribedil | 25 | 50 ± 24 |

The results of Table I show that product A possess a much greater dopaminergic stimulating activity than piribedil of the apomorphinic type.

Various modifications of the compositions and method of the invention may be made without departing from the spirit or scope thereof and it is to be understood that the invention is to be limited only as defined in the appended claims.

We claim:

1. A method of stimulating dopaminergic activity in the treatment of neurological syndromes of extrapyramidal origin in warm-blooded animals comprising administering to warm-blooded animals an dopaminergically effective amount of a member of the group consisting of N-(3,4-methylenedioxy-benzyl)-N'-(2-pyridyl)-piperazine and a non-toxic, pharmaceutically acceptable acid additional salt thereof and an inert pharmaceutical carrier.

2. A method of treating the symptoms of Parkinson disease in humans comprising administering to humans an dopaminergically effective amount of a member of the group consisting of N-(3,4-methylenedioxybenzyl)-N'-(2-pyridyl)-piperazine and a non-toxic, pharmaceutically, acceptable salt addition salt thereof and an inert pharmaceutical carrier.

3. The method of claim 2 wherein the active compound is N-(3,4-methylenedioxy-benzyl)-N'-(2-pyridyl)-piperazine.